United States Patent [19]
Raad et al.

[11] Patent Number: 5,324,275
[45] Date of Patent: Jun. 28, 1994

[54] ANTIMICROBIAL MEDICAL DEVICES

[75] Inventors: Issam I. Raad, Houston; Gerald P. Bodey, The Woodlands; Alfonso Zermeno, Houston, all of Tex.

[73] Assignee: Board of Regeants, University of Texas System, Austin, Tex.

[21] Appl. No.: 956,642

[22] Filed: Oct. 2, 1992

[51] Int. Cl.$^5$ ............................................. A61M 5/32
[52] U.S. Cl. .................................... 604/265; 604/20; 604/21
[58] Field of Search .................. 604/20, 21, 114, 265

[56] References Cited

U.S. PATENT DOCUMENTS

| 4,411,648 | 10/1983 | Davis et al. | 604/21 |
| 4,569,673 | 2/1986 | Tesi | 604/265 |
| 4,776,334 | 10/1988 | Prionas | 128/303.1 |
| 4,847,049 | 7/1989 | Yamamoto | 422/24 |
| 4,906,238 | 3/1990 | Greenfield et al. | 604/265 |
| 4,973,320 | 11/1990 | Brenner et al. | 604/265 |
| 5,071,407 | 12/1991 | Termin et al. | 604/104 |

OTHER PUBLICATIONS

Spadaro et al., "Anitbacterial Effects of Silver Electrodes with Weak Direct Current," 6 *Antimicrobial Agents and Chemotherapy* 637-642, Nov. 1974.

Berger et al., "Electrically Generated Silver Ions: Quantitative Effects on Bacterial and Mammalian Cells," 9 *Antimicrobial Agents and Chemotherapy* 357-358, Feb. 1976.

Maki et al., "An Attachable Silver-Impregnated Cuff for Prevention of Infection with Central Venous Catheter: A Prospective Randomized Multicenter Trail," 85 *The American Journal of Medicine* 307-314, Sep. 1988.

Flowers et al., "Efficacy of an Attachable Subcutaneous Cuff for the Prevention of Intravascular Catheter-Related Infection," 261 *Journal of the American Medical Association* 878-883, Feb. 10, 1988 Commerical VitaCuff®, in publication since approx. 1988.

*Primary Examiner*—Jerome L. Kruter

[57] ABSTRACT

A catheter assembly is described which comprises a catheter tube, an exterior portion of which is circumferentially surrounded by at least two parallel elongated helical conductive elements which may be operably connected to a first power source to create a first open circuit to induce an antimicrobial effect in the area proximate the exterior conductive elements through oligodynamic activity. The catheter assembly further comprises a hub at its proximal end having a cap containing a second power source. At least two internal conductive elements are disposed along the internal length of the hub and are operably connected to the second power source upon closure of the hub with the cap to create a second open circuit which creates an antimicrobial effect proximate the hub through oligodynamic activity.

12 Claims, 2 Drawing Sheets

ANTIMICROBIAL MEDICAL DEVICES

FIELD OF THE INVENTION

This present invention relates to novel antimicrobial devices. More specifically this invention relates to improved clinical catheters and indwelling devices.

BACKGROUND OF THE INVENTION

Intrusive medical devices such as central venous catheters (CVCs), urinary catheters and endotracheal catheters may introduce infection into hospitalized patients when used since the devices are subject to microbial colonization. The most common source for catheter colonization is the patient's skin, whereby organisms migrate from the skin along the intercutaneous catheter segment and ultimately enter the bloodstream and can create serious infections.

The most common organisms causing these infectious complications are *Staphylococcus epiderimidis* and *Staphylococcus aureus*. In the case of vascular catheters, these two organisms account for almost 70–80% of all infectious organisms, with *Staphylococcus epidermidis* being the most common organism. *Candida albicans*, a fungal agent, account for about 10–15% of catheter infections. A number of studies have revealed that organisms such as *Staphylococcus epidermidis* send projections into small defects in the polypropylene material, which is used in catheters. Protection against infection is particularly desirable at or around the catheter insertion point to limit entrance of organisms into the intercutaneous tunnel.

A second area in which antimicrobial measures are desirable is that of the catheter's proximal hub through which fluids enter or exit the catheter. The hub may be vulnerable to hub-related luminal and skin-related extraluminal colonization. Although the hub is normally sealed against infection to some degree by mechanical means, such as a cap or other fitting, infectious microbes may enter the catheter when this fitting is removed. Further, if the cap is fitted poorly, microbes may migrate across the intended seal. It is estimated that up to 20% of catheter-related infections begin around the catheter hub.

DESCRIPTION OF RELATED ART

The use of antimicrobial creams or other coatings, such as Chlorhexidine, may not provide an effective countermeasure to catheter-related infections, particularly over the long term. The coatings may themselves be contaminated or the microbes may develop enzymatic resistance to the medication within the coating.

Heavy metals, particularly gold, silver, and copper are known to exert, in the form of metal ions, an antimicrobial effect known as oligodynamic activity to counter infections. A number of devices have been created which employ such materials to obtain an antimicrobial effect.

A cuff has been designed which is composed of collagen impregnated with silver ions, which may be placed around a central catheter prior to catheter insertion and position subcutaneously after catheter placement. The collagen induces tissue ingrowth which seals the catheter track, and the antimicrobial activity of the silver serves as an additional barrier to organisms migrating into the catheter track. Unfortunately, due to the collagen composition, the cuff itself actually dissolves away after a period of time. Therefore, this solution is not optimal for use with patients who are catheterized for long periods of time such as cancer patients.

A urinary catheter device is also known which includes electrodes originating at the proximal end of the catheter and running along the internal length of the catheter lumen to the catheter's distal end. The catheter is adapted to accommodate current from a constant current source and transmit the current to the internal electrodes. In one embodiment, the electrodes may exit the tubular wall of the catheter near a distal end collection orifice thus exposing their surfaces to the inner lumen of the catheter. The electrodes are preferably made of a heavy metal and are ionized by the constant current source to provide for antimicrobial action.

Another bacterial barrier is known which may be used with indwelling catheters and similar medical devices which is designed to produce a circumferential zone of bacterial inhibition just within the body opening when the device is installed. The barrier is in the form of a fixed or detachable thin band, stretchable or shrinkable ring, or plastic nonconductive tape having a continuous strip of oligodynamic metal, such as silver, zinc, copper or aluminum; a more noble metal, such as platinum or gold; and a self contained current source.

While such devices are useful, they do not permit inexpensive and optimum oligodynamic activity at the exterior surface of an indwelling device such as a CVC. Accordingly, a need persists for a catheter assembly and other indwelling devices which provide effective oligodynamic activity, particularly over the long term.

SUMMARY OF THE INVENTION

In accordance with the present invention, an indwelling device is provided for helping prevent microbial infection associated with catheterization procedures. In one aspect, the invention is directed toward providing antimicrobial action for both the external and internal surfaces of catheters.

The assembly features an inexpensive, easily employed catheter assembly which has proven effective in tests for fighting infections and colonization associated with catheterization. The catheter assembly comprises a catheter tube having a distal end for intercutaneous insertion into a patient's bloodstream, urinary tract, or throat. A central exterior portion of the catheter tube is circumferentially surrounded by at least two parallel helical conductive elements which are operably connected to a first power source capable of energizing the exterior conductive elements to create an open circuit and induce oligodynamic activity in the area proximate the elements. As a result of the helical structure of the conductive elements, the antimicrobial effect is induced within sequential fields of oligodynamic activity along any longitudinal radial segment of said catheter tube.

In another aspect, the catheter tube's proximal end terminates in a hub through which fluid may be introduced or withdrawn from the catheter tube. At least two internal conductive elements are disposed along the internal length of the hub portion. The hub's cap is fitted with a small power source which energizes the internal conductive elements along the hub when said hub is closed by said cap.

A long term microbicidal effect is considered to be provided by devices constructed in accordance with the present invention since the oligodynamic activity should persist so long as the conductive elements are energized by their power sources.

DETAILED DESCRIPTION OF PREFERRED EMBODIMENTS

It is observed at the outset that a number of types of catheters may be used in constructing catheter assemblies in accordance with the present invention. Among these are central venous catheters (CVCs), urinary catheters and endotracheal catheters.

Figure 1:
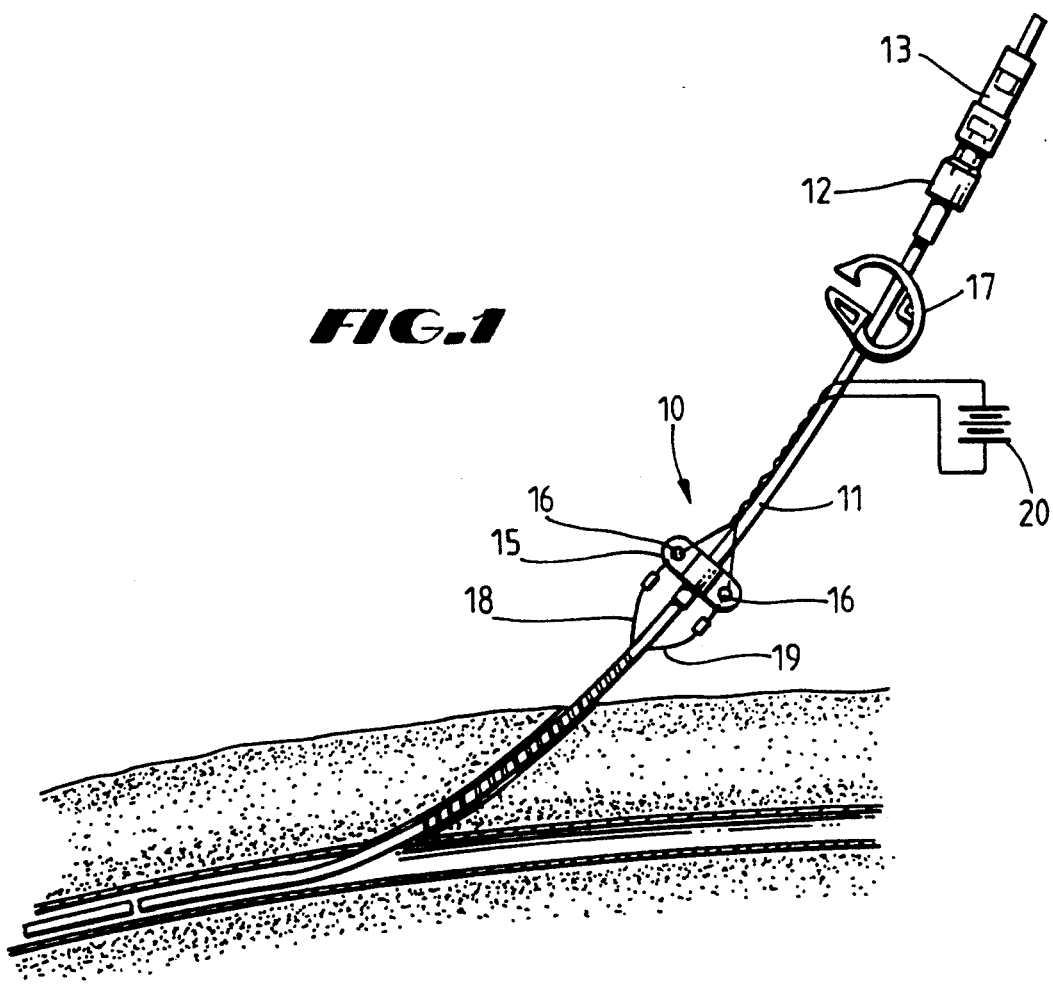
FIG. 1 shows an exemplary catheter constructed in accordance with the present invention emplaced during intravenous therapy.

Referring now to FIG. 1 there is shown an exemplary catheter assembly 10 of the CVC type comprising a catheter tube 11 of the type well known in the art adapted to be inserted intercutaneously by its distal end at a catheter insertion point and into the blood vessels of a patient. The proximal end of the catheter tube 11 terminates in a hub 12. Hub 12 typically comprises a controllable orifice useful for the introduction and removal of fluids through the catheter tube 11. Normally, hub 12 is be fitted with a removable cap 13 to provide for added sanitary conditions. The use of such caps is common in the art to prevent contamination of the interior portions of hub 12 when the cap 13 is in place.

Catheter tube 11 may be fitted along its length with one or more wing members 15 having one or more apertures 16 through portions of the surface of wing member 15. Wing member 15 is known to be useful for attachment of the catheter assembly to the skin of a patient with the aid of suture, tape, or similar attachment means.

Catheter tube 11 may also be fitted with one or more clips 17, which may be engaged or disengaged by an operator as necessary to control fluid flow throughout catheter tube 11.

Elongated conductive elements 18 and 19 are disposed so as to helically surround a central exterior portion of catheter tube 11. As may be seen in FIG. 1, elements 18 and 19 should be substantially parallel to each other and in a spaced relation to each other such that the elements do not cross or touch one another at any point along their lengths. Optimal spacing between elements 18 and 19 should be 1 cm or less. Both conductive elements 18 and 19 should be substantially comprised of a material which is electrically conductive and has good oligodynamic properties. Heavy metals, including gold, silver, platinum, iron, aluminum, zinc and copper are recommended. Copper is particularly preferred because of its combination of affordability, ductility, and demonstrated antimicrobial effectiveness.

Figure 2:
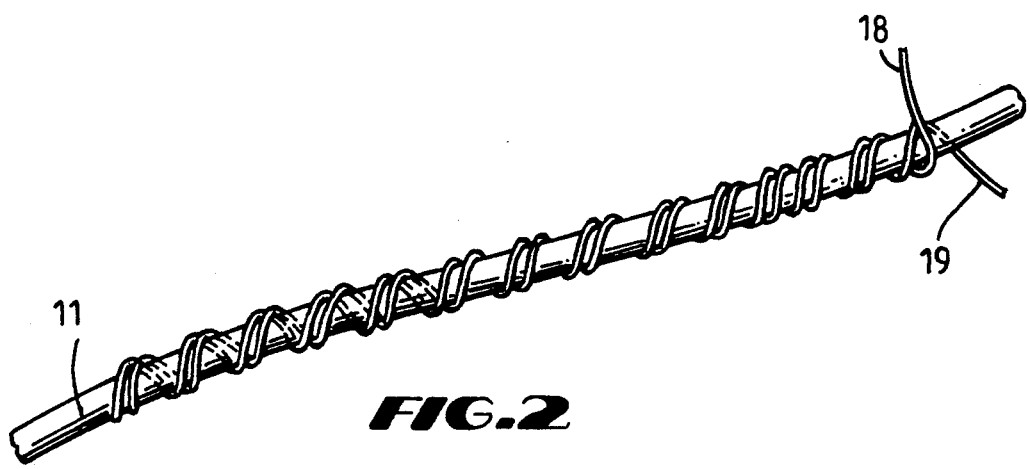
FIG. 2 details an exemplary external placement arrangement for elongated helical elements around portions of the circumference of a catheter tube.

As is best shown in FIG. 2, elements 18 and 19 may comprise thin wires formed of one of these materials and wound in a helical fashion around a central portion of catheter tube 11. In an alternative embodiment, elements 18 and 19 may comprise substrate-type metal layers which have been deposited on the surface of the catheter tube 11.

Preferably elements 18 and 19 are fixedly disposed upon the exterior surface of catheter tube 11 to ensure that these elements are not shifted along catheter tube 11 during placement or removal of the catheter assembly 10. If elements 18 and 19 comprise wires, fixed disposition may be accomplished by partially embedding the wires within the surface of the catheter tube 11 such that portions of the elements remain exposed to the exterior environment.

Toward their proximal ends, elements 18 and 19 may be operably connected to a first power source 20. Preferably, such operable connection is also reversible so that the first power source 20 may be disconnected when not in use. In a preferred embodiment, first power source 20 comprises a battery source, such as a 9 volt battery. The operable connection may be made by means of a snap-on cap 21 such as is well known for use with such batteries. When first power source 20 is operably connected to elements 18 and 19 to energize both elements, element 18 is in contact with the positive terminal of power source 20 to become positively charged. Element 19 is in contact with the negative terminal of power source 20 to become negatively charged. Since elements 18 and 19 do not contact each other, an incomplete or open circuit is created. When those portions of catheter assembly 10 come into contact with an electrolyte-containing fluid, such as the bodily fluid or moisture of a patient's body, the circuit is completed to a degree. Oligodynamic activity results from the transfer of ions between elements 18 and 19 through this fluid. The oligodynamic activity induces a concomitant antimicrobial effect proximate the area between elements 18 and 19. As a result of the helical structure of the elements 18 and 19 the antimicrobial effect is induced within sequential fields of oligodynamic activity along any longitudinal radial segment of said catheter tube. The antimicrobial effect produced by catheter assembly 10 is considered to persist for as long as elements 18 and 19 remain energized. For this reason, catheter assembly 10 is considered to provide long term microbicidal action.

A second aspect of catheter assembly 10 is directed toward providing oligodynamic activity within and around the catheter assembly's hub 12. Internal conductive elements 22 and 23 are disposed in a parallel spaced relation from each other within hub 12 along portions of the internal length of the hub 12. Elements 22 and 23 may comprise wires, radially curved strips or members of other shapes suitable to fit within the confines of hub 12's internal passageway. The spacing and composition of elements 22 and 23 should be similar to that of elements 18 and 19. If desired, elements 22 and 23 may be partially embedded within the interior surface of hub 12. However, portions of both elements 22 and 23 must remain exposed to the internal passageway of hub 12.

Figure 3:
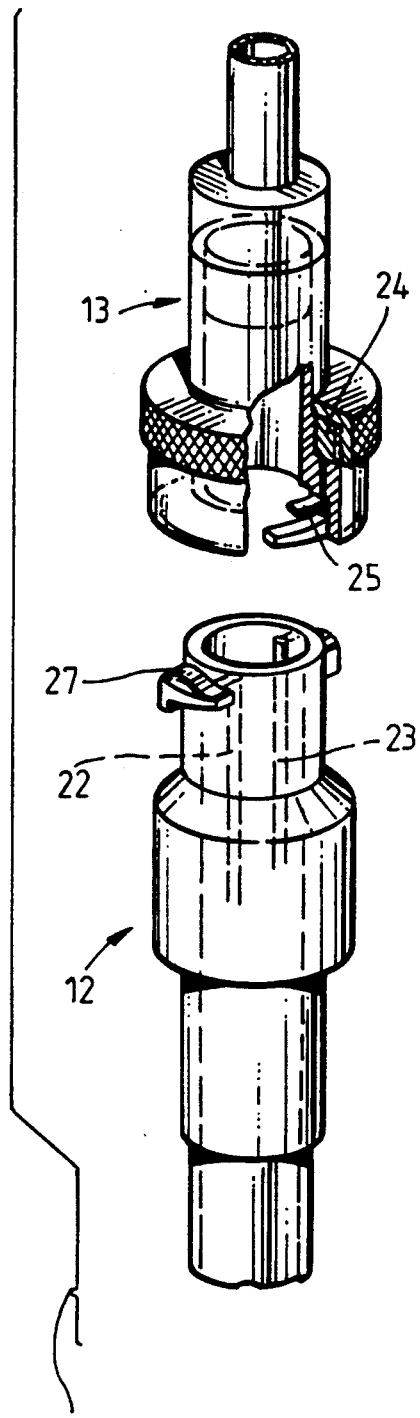
FIGS. 3 through 5 show an exemplary hub and removable cap arrangement.
Figure 4:
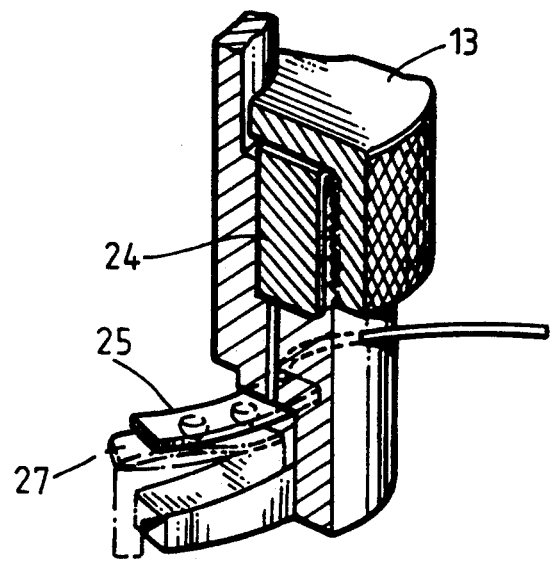
Figure 5:
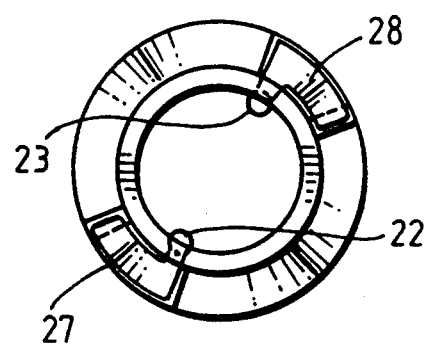

Referring now to FIGS. 3-5, second power source 24 is preferably contained within cap 13. Preferably as well, second power source 24 comprises a battery source. A small annular battery, like that exemplified in FIGS. 3 and 4, is useful as second power source 24. Alternatively, a disc-shaped battery such as that used in cameras and other devices may be emplaced somewhere in the housing of cap 13. Second power source 24 is adapted to energize elements 22 and 23 upon closure of hub 12 with cap 13. Means for accomplishing this include the use of two connectors 25 and 26, such as wires or metal strips, which extend respectively from the positively and negatively charged portions of second power source 24 to contact a pair of leads 27 and 28, each of which are associated with either element 22 or 23. When hub 12 is closed with cap 13, one connector 25 contacts lead 27 (see, e.g. FIG. 4) while the other connector 26 contacts lead 28. Thus, when hub 12 is closed with cap 13, a second open circuit is created. As with the first open circuit, fluid within hub 12 will complete the second open circuit to induce oligodynamic activity proximate elements 22 and 23 with a concomitant antimicrobial effect.

For optimal results using catheter assembly 10, the distal end of catheter tube 11 should be inserted into a catheter wound, through an intercutaneous area, and enter the intravascular portion of a blood vessel. The portion of catheter assembly 10 which is helically surrounded by external conductive elements 18 and 19 should be partially disposed within the intercutaneous area and preferably not enter the intravascular area. Preferably, the helically surrounded portion of catheter assembly 10 extends outside the catheter wound.

Controlled tests were conducted of the antimicrobial efficacy of a catheter assembly constructed in accordance with the present invention. An in vitro test model simulating an indwelling CVC was made from two petri dishes whose interior portions were connected by a narrow plastic tunnel. The first petri dish (dish A) represented a contaminated external environment. The second petri dish (dish B) simulated the intravascular area into which the tip of a CVC would penetrate. The tunnel represented the intercutaneous portion of a catheter wound leading from the external environment to the intravascular area. A sterile CVC-type catheter was capped at its proximal end and placed into the dishes such that the proximal portion resting in dish A. The central portion of the catheter was passed through the plastic tunnel until the distal portion of the catheter rested in dish B.

Prior to placement into the dishes, the catheter had been prepared such that a pair of narrow gage copper wires, like those normally connected to a 9 volt battery, were disposed helically in a parallel relation to each other along the central length of the catheter. Toward the proximal end of the catheter, portions of these wires had been encased in a plastic covering to prevent contact between the wires. The plastic covering had been stripped from distal portions of both wires beginning at a point inside of dish A which corresponded to a point just outside the catheter wound. The stripped sections of the wires had been wound helically around several inches of the catheter's central portion. During preparation, care was taken to ensure that the stripped wire sections did not touch one another. The proximal ends of the wires were connected to a 9 volt battery such that one wire attached to the positive terminal and the other wire attached to the negative terminal.

To simulate a contaminated environment, 0.1 ml of $4.0 \times 10^3$ colony forming units (CFU)/ml of a slime-producing Staphylococcus epidermidis was added to 50 mls of saline/broth and placed in disk A. One ml of saline was placed within the tunnel, and 50 mls of sterile saline/broth solution were added to dish B.

As control measures, two in vitro control models were also constructed with identical petri dishes, tunnels and fluids. The first control model contained a catheter constructed as described for the test model except that the copper wires were not connected to a power source. The second control model contained a conventional catheter having no helical copper wire structure or power source.

The test model and two control models were incubated at 37° C. for 24 hours. At the end of that time, fluid in around the distal tip of each catheter assembly was tested for contamination. More than 1000 CFU/ml were found in dish B in both control models; no organisms were found in the test model. The test results support the conclusion that a catheter assembly constructed in accordance with the present invention has remarkable efficacy toward preventing the transmission of contaminants along the exterior surfaces of an indwelling device.

Variations of the above test were performed using tunnels of different lengths (approximately 2" to 3") as well as different organisms as contaminants. Use of the inventive catheter assembly was found to be effective for all organisms with which it was tested including Staphylococcus epidermidis, Staphylococcus aureus, fungi (Candida albicans), and gram negative bacilli (xanthomonas species). Variations of the assembly which used as few as three helical coils of wire around the catheter tube were also found to be effective.

Those skilled in the art will recognize that, while specific embodiments have been illustrated and described, various modifications and changes may be made without departing from the spirit and scope of the invention. One obvious modification would be to apply the helical copper assembly described here to a different indwelling device. Another obvious modification would be to combine first power source 20 and second power source 24 into a single power source. Other similar obvious modifications not departing from the scope of the invention are readily apparent.

What is claimed is:

1. A catheter assembly comprising:
    (a) a catheter tube having a proximal end and a distal end to transmit fluid therethrough;
    (b) a hub at the proximal end of said catheter tube to permit fluid flow through said catheter tube;
    (c) at least two elongated external conductive elements fixedly disposed to be in a substantially parallel spaced relation to each other along their entire lengths and to helically surround the exterior circumference of a central portion of said catheter tube, said elements forming portions of an open circuit means upon application of power to said elements, said open circuit means inducing an antimicrobial effect through oligodynamic activity.

2. The catheter assembly of claim 1 wherein said elongated external conductive elements may be operably connected toward their proximal ends to power to form said open circuit means.

3. The catheter assembly of claim 2, wherein said elongated external conductive elements are substantially comprised of a heavy metal of the group consisting of gold, silver, platinum, iron, aluminum, zinc and copper.

4. The catheter assembly of claim 3, wherein said elongated external conductive elements are substantially comprised of copper.

5. The catheter assembly of claim 1 wherein said power is provided by a battery source.

6. The catheter assembly of claim 1, wherein said hub further comprises:
    (a) A cap adapted to removably seal said hub;
    (b) at least two internal conductive elements disposed in a parallel spaced relation from each other along portions of the internal length of said hub, said internal conductive elements to be energized by an operably connected power source to create a second open circuit means, said second open circuit means inducing antimicrobial effect in the area proximate said hub through oligodynamic activity.

7. The catheter assembly of claim 6, wherein said cap contains a power source which becomes operably connected to said internal conductive elements to create said second open circuit means upon closure of said hub with said cap.

8. The catheter assembly of claim 7 wherein said power source comprises a battery source.

9. The catheter assembly of claim 6 wherein said internal conductive elements are substantially comprised of a material in the group consisting of gold, silver, platinum, iron, aluminum, zinc and copper.

10. The catheter assembly of claim 6, wherein said internal conductive elements are substantially comprised of copper.

11. A catheter assembly comprising:
  (a) a catheter tube having a proximal end and a distal end to transmit fluid therethrough.
  (b) a hub at the proximal end of said catheter tube to permit fluid flow through said catheter tube;
  (c) at least two elongated external conductive elements fixedly disposed to be substantially parallel to each other along their entire length and helically surrounding the exterior circumference of a portion of said catheter tube, said elements forming portions of a first open circuit means upon application of power to said elements to induce an antimicrobial effect along portions of the exterior surface of said catheter tube through oligodynamic activity;
  (d) a cap adapted to removably seal said hub;
  (e) at least two internal conductive elements disposed in a parallel spaced relation from each other along portions of the internal length of said hub, said elements being energizable by power to create a second open circuit means, said second open circuit means inducing antimicrobial effect in the area proximate said hub through oligodynamic activity;
  (f) a first power source which may be operably connected to apply power to said elongated external conductive elements to create said first open circuit means;
  (g) a second power source contained within said cap, said second power source being operably connected to apply power to said internal conductive elements to create said second open circuit means upon closure of the hub with said cap.

12. The catheter assembly of claim 11 wherein said antimicrobial effect is induced within sequential fields of oligodynamic activity along any longitudinal radial segment of said catheter tube.

* * * * *